(12) United States Patent
Lorsbach et al.

(10) Patent No.: US 8,709,458 B2
(45) Date of Patent: Apr. 29, 2014

(54) SYNERGISTIC FUNGICIDAL INTERACTIONS OF 5-FLUOROCYTOSINE AND OTHER FUNGICIDES

(75) Inventors: Beth Lorsbach, Indianapolis, IN (US); W. John Owen, Carmel, IN (US); Chenglin Yao, Westfield, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/307,322

(22) Filed: Nov. 30, 2011

(65) Prior Publication Data

US 2012/0157485 A1 Jun. 21, 2012

Related U.S. Application Data

(60) Provisional application No. 61/423,857, filed on Dec. 16, 2010.

(51) Int. Cl.
*A01N 43/54* (2006.01)
*A01N 43/56* (2006.01)
*A01N 43/653* (2006.01)
*A01N 55/02* (2006.01)
*A01P 3/00* (2006.01)

(52) U.S. Cl.
USPC ........... 424/405; 504/118; 504/189; 504/209; 504/313; 504/272; 504/275; 504/244; 504/191; 504/235

(58) Field of Classification Search
USPC .......... 424/405; 504/118, 189, 209, 272, 275, 504/244, 191, 235, 313
See application file for complete search history.

(56) References Cited

U.S. PATENT DOCUMENTS

2004/0229801 A1* 11/2004 Kawabe et al. ................. 514/12
2009/0253708 A1 10/2009 Kelly et al.
2010/0029482 A1 2/2010 Benko et al.

FOREIGN PATENT DOCUMENTS

WO WO2010/047866 A2 4/2010

OTHER PUBLICATIONS

International search report for PCT/US11/62547, Apr. 6, 2012.

* cited by examiner

*Primary Examiner* — Fereydoun G Sajjadi
*Assistant Examiner* — Alma Pipic
(74) *Attorney, Agent, or Firm* — C. W. Arnett

(57) ABSTRACT

A fungicidal composition containing a fungicidally effective amount of a) a compound of Formula I and (b) at least one fungicide selected from the group consisting of myclobutanil, fenbuconazole, difenoconazole, trifloxystrobin, pentiopyrad, fluopyram, boscalid, mancozeb, and pyrimethanil provides synergistic control of selected fungi.

7 Claims, No Drawings

SYNERGISTIC FUNGICIDAL INTERACTIONS OF 5-FLUOROCYTOSINE AND OTHER FUNGICIDES

CROSS REFERENCE TO RELATED APPLICATIONS

This application claims the benefit of U.S. Provisional Patent Application Ser. No. 61/423,857 filed Dec. 16, 2010, which is expressly incorporated by reference herein.

FIELD OF THE INVENTION

This invention concerns a synergistic fungicidal composition containing (a) a compound of Formula I and (b) at least one fungicide selected from the group consisting of myclobutanil, fenbuconazole, trifloxystrobin, penthiopyrad, bixafen, fluopyram, boscalid, mancozeb, and pyrimethanil.

BACKGROUND OF THE INVENTION

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value of the crop. In most situations, the increase in value of the crop is worth at least three times the cost of the use of the fungicide.

However, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less.

Synergism occurs when the activity of two or more compounds exceeds the activities of the compounds when used alone.

SUMMARY OF THE INVENTION

It is an object of this invention to provide synergistic compositions comprising fungicidal compounds. It is a further object of this invention to provide processes that use these synergistic compositions. The synergistic compositions are capable of preventing or curing, or both, diseases caused by fungi of the class Ascomycetes. In addition, the synergistic compositions have improved efficacy against the Ascomycete pathogens, including apple scab. In accordance with this invention, synergistic compositions are provided along with methods for their use.

DETAILED DESCRIPTION OF THE INVENTION

The present invention concerns a synergistic fungicidal mixture comprising an fungicidally effective amount of (a) a compound of Formula I and (b) at least one fungicide selected from the group consisting of myclobutanil, fenbuconazole, trifloxystrobin, penthiopyrad, bixafen, fluopyram, boscalid, mancozeb, and pyrimethanil.

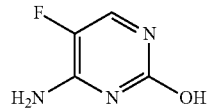

I

Bixafen is the common name for N-(3',4'-dichloro-5-fluoro[1,1'-biphenyl]-2-yl)-3-(difluoromethyl)-1-methyl-1H-pyrazole-4-carboxamide. Its fungicidal activity is described in http://www.agropages.com. Bixafen was developed to control cereal diseases.

Boscalid is the common name for 2-chloro-N-(4'-chloro[1,1'-biphenyl]-2-yl)-3-pyridinecarboxamide. Its fungicidal activity is described in *The Pesticide Manual*, Fourteenth Edition, 2006. Boscalid provides control of powdery mildew, *Alternaria* spp., *Botrytis* spp., *Sclerotinia* spp. and *Monilia* spp. on a range of fruit and vegetables.

Fenbuconazole is the common name for α-[2-(4-chlorophenyl)ethyl]-α-phenyl-1H-1,2,4-triazole-1-propanenitrile. Its fungicidal activity is described in *The Pesticide Manual*, Fifteenth Edition, 2009. Fenbuconazole provides control of a wide range of fungal pathogens on a variety of fruits, vegetables and field crops.

Fluopyram is the common name for N-[2-[3-chloro-5-(trifluoromethyl)-2-pyridinyl]ethyl]-2-(trifluoromethyl)benzamide. Its fungicidal activity is described in *The Pesticide Manual*, Fifteenth Edition, 2009. Fluopyram provides control of grey mold, powdery mildew and sclerotinia and monilinia diseases in a variety of fruits, vegetables and field crops.

Mancozeb is the common name for [[2-[dithiocarboxy)amino]ethyl]carbamodithioato(2-)-κS,κS']manganese mixture with [[2-[dithiocarboxy)amino]ethyl]carbamodithioato (2-)-κS,κS']zinc. Its fungicidal activity is described in *The Pesticide Manual*, Fifteenth Edition, 2009. Mancozeb provides control of a wide range of fungal pathogens on a variety of fruits, vegetables and field crops.

Myclobutanil is the common name for α-butyl-α-(4-chlorophenyl)-1H-1,2,4-triazole-1-propanenitrile. Its fungicidal activity is described in *The Pesticide Manual*, Fifteenth Edition, 2009. Myclobutanil provides control of Ascomycetes, Fungi Imperfecti and Basidiomycetes on a wide variety of crops.

Pyrimethanil is the common name for 4,6-dimethyl-N-phenyl-2-pyrimidinamine. Its fungicidal activity is described in *The Pesticide Manual*, Fifteenth Edition, 2009. Pyrimethanil provides control of grey mold and fruit scab on a variety of fruits and vines.

Penthiopyrad is the common name for N-[2-(1,3-dimethylbutyl)-3-thienyl]-1-methyl-3-(trifluoromethyl)-1H-pyrazole-4-carboxamide. Its fungicidal activity is described in *The Pesticide Manual*, Fourteenth Edition, 2006. Penthiopyrad provides control of rust and Rhizoctonia diseases, as well as grey mold, powdery mildew and apple scab.

In the composition of this invention, the weight ratio of the compound of Formula I to myclobutanil at which the fungicidal effect is synergistic lies within the range of between about 1:5 and about 5:1. The weight ratio of the compound of Formula I to fenbuconazole at which the fungicidal effect is synergistic lies within the range of between about 1:5 and about 5:1. The weight ratio of the compound of Formula I to trifloxystrobin at which the fungicidal effect is synergistic lies within the range of between about 1:5 and about 5:1. The weight ratio of the compound of Formula I to penthiopyrad at which the fungicidal effect is synergistic lies within the range of between about 1:5 and about 5:1. The weight ratio of the compound of Formula I to bixafen at which the fungicidal effect is synergistic lies within the range of between about 1:5 and about 5:1. The weight ratio of the compound of Formula I to fluopyram at which the fungicidal effect is synergistic lies within the range of between about 1:5 and about 5:1. The weight ratio of the compound of Formula I to boscalid at which the fungicidal effect is synergistic lies within the range of between about 1:20 and about 1:1. The weight ratio of the compound of Formula I to mancozeb at which the fungicidal effect is synergistic lies within the range of between about 1:200 and about 1:1. The weight ratio of the compound of Formula I to pyrimethanil at which the fungicidal effect is synergistic lies within the range of between about 1:20 and about 1:1.

The rate at which the synergistic composition is applied will depend upon the particular type of fungus to be controlled, the degree of control required and the timing and method of application. In general, the composition of the invention can be applied at an application rate of between about 210 grams per acre (g/acre) and about 2050 g/acre based on the total amount of active ingredients in the composition. Myclobutanil is applied at a rate between about 10 g/acre and about 50 g/acre and the compound of Formula I is applied at a rate between about 10 g/acre and about 50 g/acre. Fenbuconazole is applied at a rate between about 10 g/acre and about 50 g/acre and the compound of Formula I is applied at a rate between about 10 g/acre and about 50 g/acre. Trifloxystrobin is applied at a rate between about 10 g/acre and about 50 g/acre and the compound of Formula I is applied at a rate between about 10 g/acre and about 50 g/acre. Penthiopyrad is applied at a rate between about 10 g/acre and about 50 g/acre and the compound of Formula I is applied at a rate between about 10 g/acre and about 50 g/acre. Bixafen is applied at a rate between about 10 g/acre and about 50 g/acre and the compound of Formula I is applied at a rate between about 10 g/acre and about 50 g/acre. Fluopyram is applied at a rate between about 10 g/acre and about 50 g/acre and the compound of Formula I is applied at a rate between about 10 g/acre and about 50 g/acre. Boscalid is applied at a rate between about 50 g/acre and about 200 g/acre and the compound of Formula I is applied at a rate between about 10 g/acre and about 50 g/acre. Mancozeb is applied at a rate between about 200 g/acre and about 2000 g/acre and the compound of Formula I is applied at a rate between about 10 g/acre and about 50 g/acre. Pyrimethanil is applied at a rate between about 50 g/acre and about 200 g/acre and the compound of Formula I is applied at a rate between about 10 g/acre and about 50 g/acre The components of the synergistic mixture of the present invention can be applied either separately or as part of a multipart fungicidal system.

The synergistic mixture of the present invention can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis (dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compositions of the present invention are preferably applied in the form of a formulation comprising a composition of (a) a compound of Formula I and (b) at least one fungicide selected from the group consisting of myclobutanil, fenbuconazole, trifloxystrobin, penthiopyrad, bixafen, fluopyram, boscalid, mancozeb, and pyrimethanil, together with a phytologically acceptable carrier.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water-suspendable, or emulsifiable formulations are solids, usually known as wettable powders, or liquids, usually known as emulsifiable concentrates, aqueous suspensions, or suspension concentrates. The present invention contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water-dispersible granules, comprise an intimate mixture of the synergistic composition, a carrier and agriculturally acceptable surfactants. The concentration of the synergistic composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 1% to about 50% by weight, in a suitable liquid, based on the total weight of the emulsifiable concentrate formulation. The components of the synergistic compositions, jointly or separately, are dissolved in a carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil soluble salts or sulfated polyglycol ethers and appropriate salts of phosphated polyglycol ether.

Representative organic liquids which can be employed in preparing the emulsifiable concentrates of the present invention are the aromatic liquids such as xylene, propyl benzene fractions, or mixed naphthalene fractions, mineral oils, substituted aromatic organic liquids such as dioctyl phthalate, kerosene, dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as a granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from 0.01 percent to 1.0 percent volume/volume (v/v) based on a spray-volume of water, preferably 0.05 to 0.5 percent. Suitable adjuvant surfactants include ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present invention in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

The present invention includes within its scope methods for the control or prevention of fungal attack. These methods comprise applying to the locus of the fungus, or to a locus in which the infestation is to be prevented (for example applying to wheat or barley plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition is applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition is applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect particularly for agricultural use. The synergistic composition is particularly effective for use with agricultural crops and horticultural plants, or with wood, paint, leather or carpet backing.

In particular, the synergistic composition is effective in controlling a variety of undesirable fungi that infect useful plant crops. The synergistic composition can be used against a variety of Ascomycete fungi, including for example the following representative fungi species: leaf blotch of wheat (*Mycosphaerella graminicola*; anamorph: *Septoria tritici*; Bayer code SEPTTR); glume blotch of wheat (*Leptosphaeria nodorum*; Bayer code LEPTNO; anamorph: *Stagonospora nodorum*); spot blotch of barley (*Cochliobolus sativum*; Bayer code COCHSA; anamorph: *Helminthosporium sativum*); leaf spot of sugar beets (*Cercospora beticola*; Bayer code CERCBE); leaf spot of peanut (*Mycosphaerella arachidis*; Bayer code MYCOAR; anamorph: *Cercospora arachidicola*); cucumber anthracnose (*Glomerella lagenarium*; anamorph: *Colletotrichum lagenarium*; Bayer code COLLLA); apple scab (*Venturia inaequalis*; Bayer code VENTIN); and black sigatoka disease of banana (*Mycosphaerella fijiensis*; BAYER code MYCOFI). It will be understood by those in the art that the efficacy of the synergistic compositions for one or more of the foregoing fungi establishes the general utility of the synergistic compositions as fungicides.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease-inhibiting and phytologically acceptable amount. The term "disease-inhibiting and phytologically acceptable amount" refers to an amount of the synergistic composition that kills or inhibits the plant disease for which control is desired, but is not significantly toxic to the plant. The exact concentration of synergistic composition required varies with the fungal disease to be controlled, the type of formulation employed, the method of application, the particular plant species, climate conditions, and the like.

The present compositions can be applied to fungi or their locus by the use of conventional ground sprayers, granule applicators, and by other conventional means known to those skilled in the art.

The following examples are provided to further illustrate the invention. They are not meant to be construed as limiting the invention.

Examples

Evaluation of Protectant Activity of Fungicide Mixtures vs. Apple Scab (*Venturia inaequalis*; Bayer Code: VENTIN Fungicide spray solutions containing 10% acetone and 100 ppm Triton X-100 were applied onto apple seedlings ('Golden Delicious') in a high-volume format. Plants were inoculated with VENTIN spore suspensions 1-day after fungicide application (1-day protectant activity). Once disease fully expressed on untreated plants, disease severity on the seedlings was assessed and activity was represented by percent of leaf area free of VENTIN infection relative to untreated plants.

Treatments consisted of fungicides, including a compound of Formula I, myclobutanil, fenbuconazole, trifloxystrobin, penthiopyrad, bixafen, fluopyram, boscalid, mancozeb, and pyrimethanil, applied either individually or as two-way mixtures with a compound of Formula I. 1% of water solution of a compound with Formula I was used in the tests. Technical grades of other materials were dissolved in acetone to make stock solutions, which were then used to perform three-fold dilutions in acetone either for each individual fungicide component or for the two-way mixtures. Desired fungicide rates were obtained after mixing dilutions with nine volumes of water containing 110 parts per million (ppm) Triton X-100. Fifteen milliliter (mL) fungicide solutions were applied onto three pots of plants using an automated booth sprayer, which utilized two 6218-1/4 JAUPM spray nozzles operating at 20 pounds per square inch (psi) set at opposing angles to cover both leaf surfaces. All sprayed plants were allowed to air-dry prior to further handling. Control plants were sprayed in the same manner with the solvent blank.

When disease fully developed on the control plants, infection levels were assessed on treated plants visually and scored on a scale of 0 to 100 percent. Percentage of disease control was then calculated using the ratio of disease on treated plants relative to control plants.

Colby's equation was used to determine the fungicidal effects expected from the mixtures. (See Colby, S. R. Calculation of the synergistic and antagonistic response of herbicide combinations. *Weeds* 1967, 15, 20-22)

The following equation was used to calculate the expected activity of mixtures containing two active ingredients, A and B:

$$\text{Expected} = A + B - (A \times B / 100)$$

A=observed efficacy of active component A at the same concentration as used in the mixture;
B=observed efficacy of active component B at the same concentration as used in the mixture.

Representative synergistic interactions are listed in the Tables 1.
% DC Obs=Percent disease control observed
% DC Exp=Percent disease control expected
Synergism factor=% DC obs/% DC exp

TABLE 1

Example of synergistic interactions in 1-day protectant test vs. apple scab (Prediction using "Colby" method)

| Fungicide mixture | Rate (ppm) | % DC obs | % DC exp | Synergism factor |
|---|---|---|---|---|
| Formula 1 + myclobutanil | 2.8 + 2.8 | 97 | 78 | 1.25 |
| Formula 1 + myclobutanil | 0.9 + 0.9 | 38 | 34 | 1.1 |
| Formula 1 + fenbuconazole | 0.9 + 0.9 | 65 | 58 | 1.12 |
| Formula 1 + fenbuconazole | 0.3 + 0.3 | 38 | 13 | 2.89 |
| Formula 1 + difenoconazole | 2.8 + 2.8 | 90 | 88 | 1.02 |
| Formula 1 + trifloxystrobin | 0.9 + 0.01 | 100 | 72 | 1.38 |
| Formula 1 + penthiopyrad | 0.9 + 0.9 | 92 | 67 | 1.37 |
| Formula 1 + penthiopyrad | 0.3 + 0.3 | 94 | 26 | 3.64 |
| Formula 1 + bixafen | 0.9 + 0.9 | 86 | 61 | 1.41 |
| Formula 1 + bixafen | 0.3 + 0.3 | 73 | 26 | 2.82 |
| Formula 1 + fluopyram | 2.8 + 2.8 | 95 | 73 | 1.31 |
| Formula 1 + fluopyram | 0.9 + 0.9 | 95 | 47 | 2.01 |
| Formula 1 + fluopyram | 0.3 + 0.3 | 59 | 23 | 2.55 |
| Formula 1 + boscalid | 2.8 + 2.8 | 93 | 85 | 1.1 |
| Formula 1 + boscalid | 0.9 + 0.9 | 84 | 58 | 1.44 |
| Formula 1 + mancozeb | 0.9 + 0.9 | 54 | 49 | 1.11 |

TABLE 1-continued

Example of synergistic interactions in 1-day protectant test vs. apple scab (Prediction using "Colby" method)

| Fungicide mixture | Rate (ppm) | % DC obs | % DC exp | Synergism factor |
|---|---|---|---|---|
| Formula 1 + mancozeb | 0.1 + 0.1 | 27 | 16 | 1.73 |
| Formula 1 + pyrimethanil | 2.8 + 2.8 | 81 | 69 | 1.17 |

What is claimed:

1. A synergistic fungicidal mixture comprising a fungicidally effective amount of a) a compound of Formula (I) and (b) at least one fungicide selected from the group consisting of myclobutanil, fenbuconazole, penthiopyrad, bixafen, fluopyram, boscalid, mancozeb, and pyrimethanil wherein the weight ratio of the compound of Formula (I) to the at least one fungicide is about 1:1

2. A fungicidal composition comprising a fungicidally effective amount of the fungicidal mixture of claim 1 and an agriculturally acceptable adjuvant or carrier.

3. The mixture of claim 1, wherein the concentration of the compound of Formula (I) is about 0.1 ppm and the concentration of mancozeb is about 0.1 ppm.

4. The mixture of claim 1, wherein the compound of Formula (I) and mancozeb provide a synergistic fungicidal effect at least 10% greater than the fungicidal effect expected from summing the fungicidal efficacy of the compound of Formula (I) at the same concentration used in the mixture and the fungicidal efficacy of mancozeb at the same concentration used in the mixture.

5. The mixture of claim 1, wherein the compound of Formula (I) and mancozeb provide a synergistic fungicidal effect at least 50% greater than the fungicidal effect expected from summing the fungicidal efficacy of the compound of Formula (I) at the same concentration used in the mixture and the fungicidal efficacy of mancozeb at the same concentration used in the mixture.

6. A synergistic fungicidal mixture comprising a fungicidally effective amount of a compound of Formula (I) and trifloxystrobin, wherein the weight ratio of the compound of Formula (I) to trifloxystrobin is 90:1

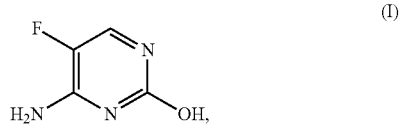

7. A fungicidal composition comprising a fungicidally effective amount of the fungicidal mixture of claim 6 and an agriculturally acceptable adjuvant or carrier.

* * * * *